United States Patent [19]

Bucovaz et al.

[11] 4,284,552

[45] Aug. 18, 1981

[54] PROCESS FOR THE PREPARATION OF COA-SPC FROM BAKERS' YEAST

[75] Inventors: Edsel T. Bucovaz; John C. Morrison; Walter D. Whybrew; Stanley J. Tarnowski, Jr., all of Memphis, Tenn.

[73] Assignee: Research Corporation, New York, N.Y.

[21] Appl. No.: 58,143

[22] Filed: Jul. 17, 1979

Related U.S. Application Data

[63] Continuation-in-part of Ser. No. 900,125, Apr. 26, 1978.

[51] Int. Cl.$^3$ .............................................. C07G 7/00
[52] U.S. Cl.$^3$ ................................. 260/112 R; 424/92
[58] Field of Search ....................... 260/112 R; 424/92

[56] References Cited

U.S. PATENT DOCUMENTS 4,160,817  7/1979  Bucovaz et al. ............. 260/112 B X

OTHER PUBLICATIONS

Life Sciences, vol. 23, pp. 2757–2768, Tarnowski et al., 1978.

Bucovaz et al., Proc. Am. Assoc. Cancer Research, 16, (1975), Abstract for Oral Presentation, p. 80.

Tarnowski et al., Abstract from 174th American Chem. Society Meeting, Aug. 28–Sep. 3, 1977.

Chem. Abstracts, vol. 89, 1978, 19771m, Bucovaz et al., Effective date 3/30/78.

*Primary Examiner*—Howard E. Schain
*Attorney, Agent, or Firm*—Oblon, Fisher, Spivak, McClelland & Maier

[57] ABSTRACT

A process for preparing CoA-SPC Bakers' yeast extract which comprises:
  lysing Bakers' yeast cells;
  separating the Bakers' yeast cell lysate into solid and supernatant fractions wherein said solid fraction is substantially free of t-factor;
  treating said solid fraction to solubilize insoluble proteinaceous material other than the insoluble CoA-SPC;
  separating said solubilized proteinaceous materials from the fraction containing said insoluble CoA-SPC; and
  contacting said fraction containing said insoluble CoA-SPC with said supernatant fraction containing t-factor to produce soluble CoA-SPC.

18 Claims, No Drawings

PROCESS FOR THE PREPARATION OF COA-SPC FROM BAKERS' YEAST

CROSS-REFERENCE TO RELATED APPLICATIONS

This application is a Continuation-in-Part of application Ser. No. 900,125, filed Apr. 26, 1978.

BACKGROUND OF THE INVENTION

1. Field of the Invention:

The present invention is directed to an improved process for the production of CoA-SPC from Bakers' yeast. CoA-SPC prepared from Bakers' yeast has found application in the preparation of reagents useful in the early diagnosis of cancer as described in United States Patent Application Ser. No. 727,633, filed Sept. 29, 1976 and now U.S. Pat. No. 4,160,817.

2. Description of the Prior Art:

Morrison et al in United States Patent Application Ser. No. 727,633, filed Sept. 29, 1976, and now U.S. Pat. No. 4,160,817 disclose and claim a method of screening individuals for the presence of cancer. This screening test has been shown to be reliable and capable of detecting cancer at a very early stage of development before any easily observable symptoms have appeared. Morrison et al discovered that the blood serum of individuals having cancer contained the B-protein associated with cancer. Thus, by simply analyzing blood serum for the B-protein it is possible to determine if an individual has cancer or not long before any visible symptoms of cancer appear.

One detection technique disclosed by Morrison et al relies upon a reagent which comprises CoA-SPC (Coenzyme A-Synthesizing Protein Complex) Bakers' yeast extract and substrates which interact with this extract to produce a binding protein. This binding protein is capable of binding to protein in the blood serum of humans to form a complex. The properties of this complex depend upon whether or not the B-protein is present. Thus, the use of this reagent provides a simple technique for screening individuals for the presence or absence of cancer.

The techniques disclosed by Morrison et al for the preparation of CoA-SPC Bakers' yeast extract produces a material containing significant quantities of impurities, in particular, other proteins which are present in the Bakers' yeast. The purification procedures described by Morrison et al are time consuming and expensive. In addition, the storage characteristics of the CoA-SPC prepared by the prior art technique is unsatisfactory. The activity of CoA-SPC stored frozen at $-20°$ C. decreases unacceptably with the passage of time.

In addition, the procedure employed by Morrison et al to produce the CoA-SPC Bakers' yeast extract requires the Bakers' yeast to be frozen in ether and subsequently thawed. As a laboratory procedure this technique is quite satisfactory, but for commercial production the handling of large quantities of ether and the resulting ether vapors present an unnecessary fire and explosion danger which are not desirable.

Tarnowski et al in an abstract distributed at the 174th American Chemical Society held Aug. 28–Sept. 3, 1977, and entitled "Preparation of the Yeast Component of the B-Protein Assay", disclosed that the CoA-SPC and other insoluble protein components of Bakers' yeast cells are solubilized by a component of the supernatant fraction. However, the CoA-SPC Bakers' yeast extract prepared by this technique contains the CoA-SPC in admixture with other proteinaceous materials.

Applicants in Application Ser. No. 900,125, filed Apr. 26, 1978, disclose and claim a method by which CoA-SPC Bakers' yeast extract may be prepared which is substantially free of the proteolytic enzymes which are found in CoA-SPC Bakers' yeast extract produced by the procedures of Morrison et al and Tarnowski et al. However, the preferred method relied upon in our earlier application for releasing CoA-SPC Bakers' yeast extract from the Bakers' yeast relied upon the use of large quantities of ether.

Accordingly, a need continues to exist for a procedure for releasing CoA-SPC Bakers' yeast extract from Bakers' yeast without the use of highly volatile and flammable chemicals and at the same time producing a CoA-SPC Bakers' yeast extract which exhibits as much activity as the extract produced through the freezing and thawing of Bakers' yeast in ether.

SUMMARY OF THE INVENTION

Accordingly, it is an object of the present invention to provide an improved method for producing CoA-SPC Bakers' yeast extract from Bakers' yeast.

It is a further object of the present invention to provide a technique for releasing CoA-SPC Bakers' yeast extract from Bakers' yeast without the use of volatile and flammable chemicals.

It is yet another object of the present invention to provide a procedure which produces a CoA-SPC Bakers' yeast extract which exhibits CoA-SPC activity without the use of volatile or flammable chemicals.

Another object of this invention is to provide a procedure for preparing CoA-SPC Bakers' yeast extract having a reduced content of other components of the Bakers' yeast, in particular, other proteinaceous materials.

Another object of this invention is to provide a procedure which produces a Bakers' yeast extract having the desired level of CoA-SPC activity in shorter processing times than was possible previously.

Still another object of the present invention is to provide a procedure for isolating from Bakers' yeast the component or components which solubilize the CoA-SPC.

Yet another object of the present invention is the characterization of the component or components which solubilize the CoA-SPC contained in Bakers' yeast cells.

Still another object of the present invention is CoA-SPC Bakers' yeast extract of high purity.

Another object of this invention is CoA-SPC Bakers' yeast extract which is substantially free of proteolytic enzymes.

Yet another object of this invention is to prepare a storage stable CoA-SPC Bakers' yeast extract.

Another object of this invention is to prepare a CoA-SPC Bakers' yeast extract which can be lyophilized and stored with only a minimal loss of activity. These and other objects of the present invention have been achieved by the following procedures:

It has now been discovered that CoA-SPC having a satisfactory purity can be prepared by lysing Bakers' yeast. The resulting liquid and solid phases are separated. The solid phase is then subjected to conditions which preferentially solubilize insoluble proteinaceous materials other than the CoA-SPC which are bound to solid phase yeast material. The resulting solubilized proteinaceous materials are separated from the solid phase containing the insoluble CoA-SPC. The CoA-SPC is solubilized by contacting this solid phase with the liquid phase which was originally formed upon thawing of the yeast. The solubilized CoA-SPC is then removed. The CoA-SPC prepared in this manner contains far less extraneous proteinaceous material than does conventionally prepared CoA-SPC.

In another embodiment of this invention the low molecular weight components of the liquid phase which results from the thawing of the Bakers' yeast are separated from the higher molecular weight components of this phase. These lower molecular weight components are then used to solubilize the CoA-SPC contained in the solid phase after it has been treated to remove other insoluble proteinaceous materials.

Yet another embodiment of this invention is the low molecular weight cellular component of Bakers' yeast which solubilizes CoA-SPC, called the t-factor.

Still a further embodiment of this invention is a process which comprises the following steps:
1. drying the Bakers' yeast;
2. grinding the Bakers' yeast until it is a powder;
3. suspending and rehydrating the Bakers' yeast powder in water;
4. releasing the Bakers' yeast extract; and
5. recovering the released CoA-SPC extract.

DETAILED DESCRIPTION OF THE PREFERRED EMBODIMENTS

In order to recover either CoA-SPC or the low molecular weight component of Bakers' yeast which solubilizes the CoA-SPC which is to be found in the Bakers' yeast cells, hereafter the "t-factor", it is necessary to lyse the yeast cells. The t-factor may be released from yeast cells by a wide variety of lysing procedures or procedures which extract cellular materials from yeast cells such as sonication, homogenization, french presses, lytic enzymes followed by osmotic shock, lyophilization and also boiling the yeast in water. In addition, the lysing techniques used to recover CoA-SPC from yeast cells may also be used to recover t-factor. Such procedures include freezing the yeast in a solvent such as ether, followed by thawing, drying the wet yeast cells, followed by rehydration, has also proven satisfactory, exposing the wet yeast cells to ether, followed by removal of the ether, has also proven satisfactory as well as enzymatic attack on the cell walls using the gut enzymes from a species of snail called *Helix pomatia*. These gut enzymes are commercially called Glusulase. Although lysing procedures which allow for the recovery of CoA-SPC from Bakers' yeast cells may be used to recover t-factor, lysing techniques which allow for the recovery of t-factor are not necessarily useful in the lysing of yeast cells when it is desired to recover CoA-SPC. While freeze-thawing by exposing the yeast to liquid nitrogen at −196° C. may be used to lyse the yeast cells when t-factor is to be recovered, such a procedure does not allow for the recovery of CoA-SPC even though the yeast cells are effectively lysed. Other lysing techniques such as freezing at −70° C. or −20° C. have also proven not satisfactory when CoA-SPC recovery is desired. In addition, freezing the yeast cells at −70° C. or in an acetone-dry ice bath followed by lyophilization and subsequent rehydration did not result in the recovery of active CoA-SPC. Similarly, wet grinding the yeast with sea sand while effective in lysing the cells did not result in an active CoA-SPC material. The use of french presses has also proven ineffective. Even when the yeast was treated with ether and then passed through the french press no active CoA-SPC was detected. Since the use of ether alone was effective in obtaining active CoA-SPC, it may be that in using the french press excessive local heat was generated thereby causing inactivation of the CoA-SPC. In addition, sonic oscillation of the yeast cells has also failed to produce an active CoA-SPC preparation. Thus, when CoA-SPC is the desired product, the proposed lysing procedure should be applied to a small sample of yeast to determine if an active CoA-SPC extract can be produced using that procedure.

Preferably, the t-factor is prepared by either (1) freezing the Bakers' yeast, preferably crumbled in liquid $N_2$ to freeze the cells and subsequently thawing them or (2) by drying and rehydrating the yeast as described subsequently in this application. A less preferred but nevertheless effective method of producing t-factor is by freezing the yeast in an ether-$CO_2$ mixture as described by Morrison et al in U.S. application Ser. No. 727,633, for the preparation of CoA-SPC.

In whichever technique is chosen, it is necessary to separate the solid and liquid phases if purified CoA-SPC Bakers' yeast extract is desired. If a purified product is not desired, the thawed material from technique (1) can be added directly to the solid portion obtained by technique (2). The rehydrated mixture of technique (2) can be directly processed to produce an impure CoA-SPC Bakers' yeast extract but this is not preferred.

When technique (2) is employed and CoA-SPC Bakers' yeast extract is also to be recovered, the separation technique must be capable of separating the t-factor which is in the liquid phase after rehydration from the solid phase which contains the insoluble CoA-SPC and other insoluble proteinaceous materials to produce the CoA-SPC containing phase which is substantially free of the t-factor. Suitable separation techniques include centrifuging, ultrafiltration, chromatography and the like. If desired, the rehydrated yeast sample may be subjected to a first separation to remove intact yeast cells by a suitable technique including decantation, low speed centrifugation and the like. The preferred separation technique involves relatively high speed centrifugation, preferably at a minimum of 4,000 to 5,000 xg, preferably at least 10,000 xg, and most preferably at about 105,000 xg or greater. The centrifuging should be conducted for a period sufficient to achieve the necessary separation. At higher centrifuging speeds this time is obviously lower than at the lower centrifuging conditions. The time can range from 10 minutes to as long as 2 hours, obviously longer centrifuging times may be used but offer no advantage. Generally, centrifuging for about one (1) hour is sufficient. If CoA-SPC Bakers' yeast extract is not to be produced or it is not desired to produce the extract in high purity, then it is not necessary to prepare a CoA-SPC containing phase which is essentially free of t-factor. Thus, in this case, less vigorous separation techniques may be used.

The supernatant fraction from the centrifugation may be used as is as the source of the t-factor to solubilize the CoA-SPC. However, it is preferred to further purify the t-factor prior to use. The additional purification may comprise denaturing followed by decanting and additional centrifuging. The denaturing is preferably achieved by heating the supernatant fraction containing the t-factor to a temperature sufficient to denature the heat denaturable components of the fraction. The temperature and time of denaturing is not critical, higher temperatures allow for shorter heating times. Typical denaturing is conducted at from 50° to 100° C. for times ranging from 3 minutes to 24 hours. Temperatures of about 80° C. for periods of about five minutes have satisfactory results. If desired, the denatured supernatant containing the t-factor may be centrifuged and then recovered. The speed of the centrifugation is not critical and may range from 5,000 xg to 105,000 xg, centrifuging at 105,000 xg or greater has proven satisfactory. The centrifuging time is not critical and may range from 10 minutes to 2 hours. Centrifuging periods of about one (1) hour have proven satisfactory. The resulting supernatant contains t-factor which is essentially free of heat denaturable proteins.

If desired, the supernatant fraction may be subjected to further treatments to increase the purity of t-factor. Such treatments can include filtration and ultrafiltration, dialysis, paper or column chromatography, precipitation or any combination thereof to yield a fraction substantially free of material having molecular weight greater than 25,000, preferably substantially free of material having a molecular weight greater than 1,000, most preferably substantially free of material having a molecular weight greater than 1,000 and less than 400. The t-factor itself has a molecular weight of less than 1,000. Based on ultrafiltration, the molecular weight is less than 500. Based on Sephadex Chromatography, the molecular weight is between 400 and 1,000. The discrepancy is probably a result of the ultrafiltration membrane having a higher molecular weight cut off than 500. The membrane has been found to allow CoA which has a molecular weight of about 800 to pass through at the same rate as a compound with a molecular weight of 500 or less. Accordingly, the molecular weight of the t-factor is most probably between 400 and 1,000.

When this technique is used to prepare the t-factor, it is possible to treat the solid material which is recovered from the initial separation of liquid and solid phase from the rehydrated yeast to recover CoA-SPC therefrom. The recovery will be subsequently described in detail.

The second procedure for preparing t-factor comprises freezing the yeast under cryogenic conditions such as by introducing the Bakers' yeast, preferably in crumbled form, into liquid nitrogen to freeze the cells. The period of the immersion in liquid nitrogen is not critical so long as it is for a time sufficient to freeze the cells. It may range from 5 minutes to 1 hour, though longer times may be used, no advantage is gained therefrom. Shorter times can be used if the cells are frozen.

The frozen cells are subsequently thawed. The thawed mixture contains lysed cells, intact cells and soluble cellular components from both. The solid and liquid fractions are separated since the t-factor is principally in the liquid phase, using conventional techniques such as centrifuging, filtering, dialyzing and the like. Preferably, the separation is achieved by centrifuging at a speed and time sufficient to achieve the separation. The speed of centrifuging is preferably at least 4,000 xg, more preferably, at least 10,000 xg, and most preferably at about 105,000 xg. The period of centrifuging is dependent upon the force. Generally, the centrifuging is performed for at least 10 minutes, preferably for at least 30 minutes. Centrifuging for one hour at 105,000 xg has proven satisfactory, although longer or shorter periods may be used.

The liquid fraction thus recovered may be used directly as the source of t-factor to solubilize the CoA-SPC in the yeast cells. Preferably, however, the supernatant fraction containing the t-factor is subjected to further purifications such as denaturing, dialysis, filtration, ultrafiltration, precipitation and chromatography. Combinations of these purification procedures may also be used. The purification procedure must be performed such that the fraction containing the low molecular weight constituents is retained since the t-factor appears to have a comparatively low molecular weight, probably 1000 or less.

The preferred purification procedure comprises first denaturing the denaturable proteins in t-factor-containing supernatant. The denaturing is most preferably accomplished by heating at temperature and time sufficient to denature the heat denaturable proteins. Generally, temperatures of from 50° to 100° C. may be used, preferably from 75° to 85° C. The period for which the mixture is heated is dependent upon the temperature, but generally ranges from 3 minutes to 24 hours. The period of heating is chosen such that the desired denaturing is obtained. At temperatures of about 80° C., heat treatment times of 5 to 10 minutes have proven satisfactory. The resulting mixture may be used as the source of t-factor to solubilize the CoA-SPC. Preferably, however, the mixture is treated to remove the denatured proteins.

The denatured proteins may be removed using conventional techniques such as centrifuging, filtering, dialysis and the like. Centrifuging is preferred because of its simplicity. The centrifuging which may be used are those employed previously to separate the liquid and solid phases. Centrifuging at about 105,000 xg for about 30 minutes has proven satisfactory.

The resulting supernatant may be used directly as the source of t-factor for the CoA-SPC solubilization. However, it is preferable to remove any high molecular components before using the supernatant as the t-factor source. Preferably, those components having a molecular weight greater than 25,000 are removed, more preferably those with a molecular weight above about 1,000 are removed. Thus, the fractions containing components with molecular weights equal to or less than 25,000 preferably of about 1,000 or less and most preferably of molecular weight of 400 to 1,000 are used as the source of t-factor. Such can be prepared using conventional techniques such as filtering, dialysis, ultrafiltration, chromatography, precipitate and combinations thereof. The exact procedure is not critical.

A typical procedure could involve dialysis against reduced pressure utilizing a membrane which retains most components having a molecular weight greater than 15,000 to 20,000. The reduced pressure is not critical and may range from 12 to 700 mm Hg. The t-factor activity is possessed by the dialysate. Alternatively, the supernatant may be filtered utilizing a medium which retains materials having a molecular weight of 25,000 or greater. The t-factor is in the filtrate. Either the dialysate or the filtrate may be used directly as the source of t-factor for the solubilization of CoA-SPC.

Preferably, the dialysate or filtrate is subjected to ultrafiltration and chromatography to remove materials having a molecular weight of greater than 1000 or less than 400. The filtrate is then utilized as the source of t-factor to solubilize the CoA-SPC. Using the techniques described it is possible to obtain t-factor of the desired purity. After simply denaturing by heating the t-factor containing supernatant as described previously, a purification of 1.5 fold is obtained. Filtering to remove from the denatured material the fraction having a molecular weight greater than 25,000 results in t-factor having a purity of about 3 fold. Unpurified t-factor may be used to solubilize the CoA-SPC from the yeast cells, however, t-factor of at least 1.5 fold purity is preferred, more preferably t-factor with a purity of at least 3 fold is used. It is possible to prepare t-factor having a purity of up to 900 fold if desired and this may be used to solubilize CoA-SPC. T-factor having a purity of from 540 to 625 fold can be readily obtained. However, such high purity t-factor is not necessary to prepare the CoA-SPC of high purity of this invention.

The t-factor purity is calculated as follows:

$$\frac{\text{Weight of total solids in crude supernatant sufficient to yield 1 ml of purified } t\text{-factor}}{\text{Total solid weight in 1 ml of recovered, purified } t\text{-factor}} = \text{fold of purity}$$

In a preferred aspect of the present invention the yeast is lysed by drying and grinding the Bakers' yeast. During drying autolysis of the yeast cells probably occurs. This autolytic process comprises the breaking down of the yeast cell wall or a portion thereof by endogenous enzymes. The yeast is dried to an extent sufficient to allow it to be ground to a fine powder. The temperature at which the yeast is dried is not critical, but it should be below the temperature at which the CoA-SPC activity is destroyed. Temperatures up to 60° C. have proven satisfactory, with temperatures below 50° C. being particularly preferred. Drying the yeast at room temperature, 20° to 25° C., has proven to be satisfactory. When room temperatures are employed, it may take, however, up to three days to dry the yeast with drying times on the order of from 40 to 48 hours not being uncommon. Temperatures as low as 10° C. are satisfactory, but at such conditions it requires a very long time to dry the yeast. In contrast, at 50° C. 24 hours is sufficient time. It is preferred to dry the yeast at temperatures between about 20° and 45° C. At the elevated temperatures and in the presence of a warm air current the drying time for the yeast may be reduced markedly. Additionally, crumbling the yeast prior to drying also speeds up the drying process. Adequate drying has been achieved when from 65 to 100 percent of the water originally present in the yeast has been removed, preferably from 85 to 100 percent of the water originally present in the yeast is removed. Particularly good results have been obtained when from 90 to 100 percent of the water has been removed. Yeast normally includes from about 68 to 70 percent water by weight as it is obtained commercially. The drying time is chosen such that the desired degree of drying is obtained. In general, the yeast need be dried only so long as it no longer has a pasty consistency and is capable of being ground to a fine powder.

If faster drying rates are desired, it is possible to dry the yeast in a vacuum while maintaining the yeast temperature at a level at which autolysis occurs, preferably from about 4° C. to 60° C., more preferably 4° to 40° C., most preferably 20° to 25° C. In this manner the drying time for the yeast may be reduced to a shorter time. In order to maintain the temperature at a level at which autolysis occurs while drying in a vacuum it may be necessary to heat the yeast, especially when high vacuums are employed.

The dried yeast either before or after drying may be stored at room temperature for several days without any detectable loss in CoA-SPC activity. Preferably, the dried yeast is stored under comparatively dry conditions in a sealed container to exclude moisture. Storage in the dry form has a distinct advantage in that significantly less material need be stored since a high percentage of the yeast is water.

After drying the yeast, one then grinds the yeast into a fine powder. Essentially any mechanical method of grinding the yeast to the desired particle size may be achieved. If only small quantities of yeast are to be ground, a mortar and pestle have been found to be quite adequate. Additionally, sandpaper discs have also been used on a laboratory scale. In addition, simply pushing the dried yeast through a mesh screen has proven also to be quite adequate. When one desires to grind large quantities of yeast, conventional mechanical means readily available may be employed such as ball mills, hammer mills and the like.

The grinding is performed for a time sufficient to achieve the desired fine particle size. The grinding is performed simply to cause additional rupture of the cell wall over and above that which has occurred as a result of autolysis during the drying step and to speed up the rehydration process. Preferably, the yeast is ground to a size less than 5.6 mm or 5600μ, preferably the yeast is ground to a particle size of less than 0.425 mm (425 μ). The yeast may be ground to as fine a particle size as one desires and good results have been achieved when the yeast is ground to between about 425μ and 38μ size.

In order to recover the CoA-SPC from the Bakers' yeast, it is necessary to hydrate the dry and ground yeast by suspending the ground yeast in water. Ordinary tap water or deionized water or the like may be used. The amount of water which is needed is not critical and it need only be enough to obtain a fluid suspension. While as much water as one desires may be used over and above that necessary to obtain a fluid suspension, the use of large excesses of water will result in excessive dilution of the CoA-SPC and would make the resulting recovery of the CoA-SPC difficult. Good results have been achieved when anywhere from ½ to 4 times the amount of water removed during drying is used to rehydrate the yeast. Preferably, from ⅔ to about twice the amount of water removed during drying is added to the dried yeast to suspend and hydrate it. The temperature at which the yeast is hydrated is not critical and may be at essentially any temperature at which the water is liquid so long as it is below the temperature at which the CoA-SPC activity of the yeast is destroyed. Preferably, the temperature of hydration is from about 4° C. to about 40° C. and preferably at about room temperature of from 10° to 20° C. In the most preferred embodiment, the dried yeast is hydrated at 4° to 10° C.

The hydrated yeast may be treated in the same manner as the thawed yeast in U.S. application Ser. No. 727,633, filed Sept. 29, 1976.

In the preferred embodiment as described in Applicants' earlier application, the hydrated yeast material is subjected to a separation technique to separate the phase containing the t-factor which is the liquid phase from the solid phase which contains the insoluble CoA-SPC along with other insoluble proteinaceous material to produce a CoA-SPC containing phase which is substantially free of t-factor. Essentially any separation technique which is capable of separating the two phases may be employed and includes centrifuging, ultrafiltration, column chromatography and the like. If desired, the hydrated yeast sample may be subjected to a first separation to remove intact yeast cells by a suitable technique such as decantation, low speed centrifugation and the like. The preferred separation technique involves relatively high speed centrifugation, preferably at a minimum of 4000 to 5000 xg, preferably at least 10,000 xg, and most preferably at about 105,000 xg or greater. The centrifuging should be conducted for a period sufficient to achieve the necessary separation. At higher centrifuging speeds, this time is obviously lower than at the lower centrifuging conditions. The time can range from 10 minutes to as long as two hours, obviously longer centrifuging times may be used, but offer no advantage. Generally, centrifuging for about one hour is adequate.

The supernatant fraction from the centrifugation may be used as is as the source of t-factor to solubilize the CoA-SPC. However, as described it is preferred to purify the t-factor prior to use.

The CoA-SPC containing phase includes not only the insoluble CoA-SPC, but also other insoluble proteinaceous materials as well as other impurities. Since the presence of the t-factor is necessary to solubilize the CoA-SPC, but not the other insoluble proteinaceous materials, it is possible to selectively solubilize these other insoluble proteinaceous components of the yeast. The solubilization can be accomplished by simple agitation, agitation in aqueous medium and the like. The rate and degree of solubilization can be increased by the addition of salts such as chlorides, nitrate, acetate and the like. Preferably an aqueous medium containing chloride ions is utilized. The cation moiety of the salt may be any cation which does not inhibit CoA-SPC activity. Thus, the salts of mercury, lead, zinc, iron and lithium should be avoided. However, other salts may be used including potassium, sodium, magnesium, calcium and manganese salts which have all been successfully utilized. In particular, KCl, NaAc, Tris buffer and the like may be used. Appropriate selection of the agitation time and anion concentration allows one to remove as much or as little of these other proteinaceous materials as may be desired. Generally, an anion, preferably chloride ion, concentrations of from 0.01 to 2.0 N have proven satisfactory, preferably from 0.026 to 1.0 N and most preferably from 0.47 to 0.73 N. Higher concentrations of anion may be used but offer no particular advantage. Regardless of the anion concentration, the active CoA-SPC is not solubilized in the absence of t-factor.

The pH of the medium during the solubilization of these other insoluble proteinaceous materials is not critical and may be acid, basic or neutral pH. Preferably the pH ranges from 5.0 to 8, most preferably from 5.6 to 5.9.

The pH may be maintained by addition of essentially any buffer, acid or base, such as tris acetate and NaAc.

The thus solubilized proteinaceous material is separated from the cellular material containing the insoluble CoA-SPC by conventional techniques such as centrifugation at 10,000 to 105,000 xg for 30 minutes, and decantation of the supernatant liquid containing the extraneous protein, filtration and the like.

The recovered cellular material may, if desired, be washed with water to remove any residual impurities or soluble proteinaceous materials not removed by the separation procedure. The washed cellular material is then introduced into an aqueous medium containing chloride or nitrate ions. The source of chloride or nitrate ions is not critical and includes those mentioned previously. The concentration of chloride or nitrate ions influences the rate at which the t-factor solubilizes the CoA-SPC. Accordingly, it is desirable to have a minimum chloride or nitrate ion concentration of 0.02 N. Lower concentrations will work but the rate of solubilization will be low. The maximum chloride or nitrate ion concentration is approximately 2 N (75 mg/ml.). Since the CoA-SPC or t-factor source or both will probably contain some endogenous chloride ions, it is not essential to add chloride or nitrate ions to the aqueous medium. It is preferred, however, to adjust the chloride ion concentration to at least 0.40 N or add sufficient nitrate ions to achieve this concentration and to achieve a satisfactory solubilization rate. Most preferably the chloride or nitrate ion concentration will range from 0.47 to 0.73 N.

The pH of the aqueous medium during the solubilization of the CoA-SPC is not critical. Preferably the pH ranges from 5 to 8, more preferably from 5 to 6, and most preferably it is from 5.6 to 5.9. The pH can be adjusted by addition of suitable acids, bases or buffers, such as NaAc and tris acetate. However, the pH need not be adjusted and water alone can be utilized in the solubilization.

The quantity of the t-factor or t-factor-containing extract which is added it not critical. However, the rate at which the CoA-SPC is solubilized is a function of the quantity of t-factor present. The amount of t-factor utilized to solubilize the CoA-SPC may be that which was recovered during the initial processing steps of the Bakers' yeast. The t-factor may be added in the form of the supernatant which was originally separated from the thawed cellular material. The total quantity of this supernatant may be added or a fraction thereof, such as ½, ¼, ⅓, ⅞, etc. In order to recover CoA-SPC having a high purity it is preferable to utilize a t-factor-containing mixture which has been purified by any of the previously described procedures.

It is possible to recover the t-factor from the solubilized CoA-SPC by dialysis or filtration through a membrane which retains components having a molecular weight greater than 100,000 MW. The filter or dialysate can then be treated to obtain purified t-factor using the procedures described previously. If desired, purified t-factor may be obtained directly by dialysis or filtration through a membrane which retains those components having a molecular weight greater than 1,000. By recovering and re-using the t-factor it is possible to use greater quantities of t-factor to solubilize CoA-SPC than are found in the original sample from which the CoA-SPC is being recovered. Thus, t-factor from as many yeast samples as one desires can be retained and used to solubilize CoA-SPC from any quantity of yeast. This procedure provides an economical technique for increasing the solubilization rate. The t-factor used to solubilize the CoA-SPC can be that obtained by procedure (2) described previously.

The CoA-SPC Bakers' yeast extract which is produced by this preferred procedure is essentially free of proteolytic enzymes. The presence of proteolytic enzymes in CoA-SPC Bakers' yeast extracts produced by the prior art procedure resulted in an extract having unsatisfactory storage characteristics. The CoA-SPC Bakers' yeast extract of this invention loses substantially less of its activity upon lypholizing and storage than the prior art extract because its reduced proteolytic enzyme content. The extract of this invention also processes superior storage characteristics when stored frozen at −20° C.

Additionally, the CoA-SPC Bakers' yeast extract of this invention requires less ATP substrate to produce the binding protein utilized in the cancer detection procedure of U.S. application Ser. No. 727,633, filed Sept. 29, 1976. Also, the CoA-SPC Bakers' yeast extract of this invention has improved CoA-SPC activity per mg/protein when compared with that previously available. CoA-SPC Bakers' yeast extract has a molecular weight of about 200,000 and is characterized by its interaction with the substrates L-cysteine, D-pantothenic acid and ATP. It is also characterized by its interaction with L-cysteine, D-pantothenic acid and ATP to produce the binding protein which is capable of complexing with blood serum protein as described in U.S. application Ser. No. 727,633, filed Sept. 29, 1976.

Having generally described this invention, a further understanding can be obtained by reference to certain specific examples which are provided herein for purposes of illustration only and are not intended to be limiting unless otherwise specified.

EXAMPLE 1

Yeast samples were dried at several temperatures and the CoA-SPC activity of the product is measured. The results shown in Table 1.

All temperatures in this Example and those which follow are expressed in Centigrade units.

TABLE II

EFFECT OF GRINDING ON THE ABILITY TO EXTRACT CoA—SPC FROM DRIED YEAST SOLIDS[d]

| Condition | CoA—SPC Activity (nmoles) | Soluble Protein (mg/ml) | Specific Activity (nmoles/mg/h) |
|---|---|---|---|
| Control[b] | 25.6 | 74 | 6.9 |
| No grinding[c] | 15.3 | 68 | 4.5 |
| Grinding with mortar and pestle[d] | 27.1 | 75 | 7.2 |
| Grinding with 1 part alumina and 9 parts dry yeast solid[e] | 29.4 | 81 | 7.3 |
| Freeze-dried yeast[f] | 0 | 81 | 0 |
| Sand paper discs[g] | 25.9 | 80 | 6.5 |

[a]Rehydration with deionized $H_2O$ (4°) equivalent to weight loss by drying 30 g compressed yeast. Following the addition of $H_2O$, the yeast was mixed 18 h at 4° with 10 mg KCl/ml yeast suspension, centrifuged at 10,000 xg for 20 minutes at 4° to recover the soluble portion.
[b]Fresh Bakers' yeast prepared by the Ether-$CO_2$ method (see Life Sciences 23:2757-2768, 1978; see U.S. Pat. application Ser. No. 900,125, filed April 26, 1978; see U.S. Pat. application Ser. No. 727,633).
[c]Dried yeast solids (34% of the original wet weight) rehydrated without grinding following the drying period.
[d]Ground for approximately 5 minutes by hand with a porcelain mortar and pestle at 24°.
[e]Alcoa chromatographic alumina F-20 not removed prior to rehydration and mixing.
[f]Compressed yeast was shell frozen and lyophilized to dryness and ground.
[g]Coarse sand paper glued to the flat surface of a disc which was attached to a drill press was used to grind the dried yeast. The dried yeast was sandwiched between two sandpaper discs and ground for 5 minutes at low speed to prevent the generation of excess heat.

EXAMPLE 3

Table III illustrates the effect of the particle size of

TABLE I

EFFECT OF DRYING TIME AND TEMPERATURE ON EXTRACTION OF CoA—SPC FROM FRESH BAKERS' YEAST

| | DRYING TEMPERATURE[+] | | | | | | | | | | | |
|---|---|---|---|---|---|---|---|---|---|---|---|---|
| | 4° | | | | 24° | | | | 50° | | | |
| | REHYDRATION TEMPERATURE[a] | | | | | | | | | | | |
| | 4° | | | | 4° | | | | 4° | | | |
| Time (h) | % Weight[b] Remaining | CoA—SPC[c] Activity (nmoles) | Soluble[d] Protein (mg/ml) | Specific Activity (nmoles/mg/h) | % Weight Remaining | CoA—SPC Activity (nmoles) | Soluble Protein (mg/ml) | Specific Activity (nmoles/mg/h) | % Weight Remaining | CoA—SPC Activity (nmoles) | Soluble Protein (mg/ml) | Specific Activity (nmoles/mg/h) |
| 12 | 95.64 | 0 | 2 | 0 | 53.00 | 9.9 | 40 | 5.0 | 33.70 | 23.5 | 68 | 6.9 |
| 24 | 91.46 | 0 | 19 | 0 | 37.70 | 13.0 | 50 | 5.2 | 31.60 | 23.5 | 69 | 6.8 |
| 36 | 87.12 | 0 | 11 | 0 | 34.00 | 21.1 | 61 | 6.9 | 31.60 | 23.5 | 69 | 6.8 |
| 48 | 83.60 | 0 | 11 | 0 | 33.70 | 23.5 | 68 | 6.9 | 31.20 | 23.5 | 63 | 7.5 |
| 60 | 78.90 | 0 | 11 | 0 | 33.90 | 21.1 | 61 | 6.9 | 31.00 | 23.5 | 64 | 7.3 |
| 72 | 74.20 | 0 | 11 | 0 | 34.10 | 21.1 | 61 | 6.9 | 31.00 | 23.5 | 50 | 9.4 |

[+]Drying was accomplished by crumbling fresh Bakers' yeast and spreading the yeast to a uniform surface in glass or plastic trays.
[a]Rehydration was accomplished utilizing deionized $H_2O$ in a volume equivalent to the weight loss during the drying process. With the notable exception that the weight lost due to moisture by the yeast dried at 4° was insufficient for mechanical mixing to be achieved when hydrated, additional deionized water was added to the paste. All dried yeast solids were ground with a porcelain mortar and pestle at 24° prior to rehydration.
[b]The initial weight of the fresh compressed Bakers' yeast was 30 g; 26 ml yeast cell volume.
[c]As described under "Assay for CoA—SPC Activity", these values listed represent the formation of [$^{35}$S]-dephospho-CoA bound to protein precipitated by TCA (Life Sciences 23:2757-2768, 1978).
[d]Soluble protein measurements are based on the Lowry method for protein estimation (J. Biol. Chem. 193:265-275, 1951).
[e]Extraction was carried out by mechanical mixing at 4° for 18 h with approximately 10 mg KCl/ml of rehydrated yeast suspension. Centrifugation followed at 10,000 xg or 105,000 xg for 20 minutes at 4° to recover the liquid portion of the rehydrated mixture.

The results obtained when using a drying temperature of 4° C. signify that inadequate drying of the yeast occurred. If the test had been allowed to continue, CoA-SPC activity would have been obtained.

EXAMPLE 2

Table II sets forth the results for various grinding procedures as well as for alternative techniques of preparing CoA-SPC from yeast.

In an early experiment the yeast was ground with 1 part alumina to 1 part yeast. No CoA-SPC activity was detected in the product prepared from this ground material. The reason for this apparently anomalous result is not known at the present time.

the ground yeast on CoA-SPC recovery.

In these experiments it was easier to obtain a suspension from the smaller particle size yeast than from the large particle size (5600-425μ).

TABLE III

EFFECT OF PARTICLE SIZE OF DRIED BAKERS' YEAST ON THE EXTRACTION[b] of CoA—SPC[a]

| Particle Size Range (microns) | CoA—SPC Activity (nmoles) | Soluble Protein (mg/ml) | Specific Activity (nmoles/mg/h) |
|---|---|---|---|
| 5600–425 | 15.3 | 68 | 4.5 |
| 425–125 | 22.7 | 76 | 6.0 |

TABLE III-continued
EFFECT OF PARTICLE SIZE OF DRIED BAKERS' YEAST ON THE EXTRACTION[b] of CoA—SPC[a]

| Particle Size Range (microns) | CoA—SPC Activity (nmoles) | Soluble Protein (mg/ml) | Specific Activity (nmoles/ mg/h) |
|---|---|---|---|
| 125-38 | 28.4 | 84 | 6.8 |

[a]Dried, unground Bakers' yeast (34% of the original wet weight) contains particles ranging from 5600 microns to 88 microns. Ground Bakers' yeast contains particles ranging from 425 microns to 38 microns. Particle sizes were determined through the use of the U.S. Standard Sieve Series, W. S. Tyler Company. Grinding was achieved by use of a porcelain mortar and pestle at 24°.
[b]Extraction of CoA—SPC was with deionized $H_2O$ at 4°, followed by mixing for 18 h at 4° with 10 mg KCl/ml of yeast suspension. The soluble portion was recovered by centrifugation at 10,000 xg for 20 minutes at 4°.

EXAMPLE 4

Table IV demonstrates that CoA-SPC activity is essentially not affected by the type of water used during hydration. It is preferred to use deionized water to insure that no detrimental contamination of the CoA-SPC occurs.

TABLE IV
CONDITION OF THE WATER FOR REHYDRATION[a] FOR THE EXTRACTION OF CoA—SPC FROM DRIED BAKERS' YEAST SOLIDS[b]

| Water Type | CoA—SPC Activity (nmoles) | Soluble Protein (mg/ml) | Specific Activity (nmoles/ mg/h) |
|---|---|---|---|
| Tap | 20.4 | 59 | 6.9 |
| Distilled | 21.1 | 61 | 6.9 |
| Milli-Q-Deionized | 21.1 | 61 | 6.9 |

[a]Water at 4° was used to reconstitute the dried ground yeast solids. The water added was equivalent to the weight lost during the drying procedure; KCl was added to a concentration of 10 mg/ml of yeast suspension; the suspension was mixed at 4° for 18 h. The soluble portion was recovered by centrifugation at 10,000 xg for 20 minutes at 4°.
[b]The dried Bakers' yeast solids (34% of the original wet weight) were ground to a particle size range of 425 to 38 microns with a porcelain mortar and pestle at 24°.

EXAMPLE 5

Table 5 demonstrates the effect of temperature on the rehydration step. As the temperature is increased above room temperature, the CoA-SPC activity begins to decrease until the deactivating temperature is reached.

TABLE V
EFFECT OF THE TEMPERATURE OF THE WATER OF REHYDRATION[a] ON THE EXTRACTION OF CoA—SPC FROM DRIED BAKERS' YEAST SOLIDS

| Water Temperature[b] (°C.) | CoA—SPC Activity (nmoles) | Soluble Protein (mg/ml) | Specific Activity (nmoles/ mg/h) |
|---|---|---|---|
| 4 | 25.6 | 74 | 6.9 |
| 24 | 25.6 | 76 | 6.7 |
| 36 | 22.5 | 75 | 6.0 |
| 50 | 18.7 | 76 | 4.9 |
| 65 | 0 | 32 | 0 |

[a]Deionized $H_2O$ (66% by weight) was added at the prescribed temperature to dried ground (particles ranged from 425 to 38 microns) Bakers' yeast solids equivalent to the weight lost during the drying procedure. KCl was added to a concentration of 10 mg/ml of yeast suspension and the suspension was mixed at 4° for 18 h. The soluble portion was recovered by centrifugation at 10,000 xg for 20 minutes at 4°.
[b]The water and dried (34% of the original wet weight) Bakers' yeast admixtures were maintained at the indicated water temperature until all solids were dissolved.

EXAMPLE 6

In the following experiments the effect of the concentration of dried Bakers' yeast solids during the rehydration of same to form a suspension on the extraction of CoA-SPC activity is determined. In Run A the results obtained when the concentration of Bakers' yeast solids was 17 wt.% appears to be an anomalous result which at the present time has not been explained. It is believed that the results obtained in Run B at the 17 wt.% concentration are more typical of those which are obtained when employing the procedure outlined in footnote a.

The reduced CoA-SPC activity which is found when using these concentrations of less than 34 wt.% appears to be caused by excessive dilution of the t-factor which is necessary to release CoA-SPC. If additional pure t-factor is added to the suspension to increase the concentration of t-factor, one will thereby obtain the release of CoA-SPC. The amount of additional t-factor to be added can be readily determined by those skilled in the art but from the experimental results presented below, it appears to be preferable to add enough t-factor so as to achieve the concentration of t-factor which is obtained when the yeast cells are diluted to about 34 wt.%. When adding additional t-factor, it is desirable that purified t-factor be used since unpurified t-factor contains a number of impurities such as cold cysteine and pantothenic acid which may inhibit the reaction of CoA-SPC in the assay procedure.

TABLE VI
EFFECT OF THE CONCENTRATION OF DRIED BAKERS' YEAST SOLIDS IN SUSPENSION ON THE EXTRACTION OF CoA—SPC ACTIVITY

| Concentration[a] (w/w %) | CoA—SPC Activity (nmoles) | Soluble Protein (mg/ml) | Specific Activity (nmoles/ mg/h) |
|---|---|---|---|
| Run A: | | | |
| 68 | 0 | 120 | 0 |
| 51 | 18.2 | 99 | 3.7 |
| 34 | 23.5 | 68 | 6.9 |
| 17 | 23.5 | 27 | 17.4 |
| 8.5 | 0 | 6 | 0 |
| Run B:[b] | | | |
| 34 | 23.5 | 68 | 6.9 |
| 20 | 4 | 27 | 3 |
| 17 | 0.9 | 14 | 1.3 |
| 15 | 0 | 13 | 0 |
| 10 | 0 | 10 | 0 |
| 8.5 | 0 | 6 | 0 |

[a]Dried Bakers' yeast solids (34% of the original wet weight) were ground with a porcelain mortar and pestle at 24° to a particle size range of 425 to 38 microns. The yeast particles were rehydrated with deionized $H_2O$ at 4° to the concentrations prescribed based on weight. KCl was added to each yeast suspension at a concentration of 10 mg/ml of yeast suspension. The yeast suspension was mixed at 4° for 18 h and the soluble portion recovered by centrifugation at 10,000 xg for 20 minutes at 4°. A normal suspension of ground Bakers' yeast solids is 34% (w/w).
[b]Average of several experiments.

EXAMPLE 7

Table VII demonstrates the results obtained when releasing the CoA-SPC from the yeast by adding a suitable source of chloride ions and stirring for 18 hours. As can be seen, lower temperatures favor a high CoA-SPC activity. At higher temperatures, short mixing times are necessary. For example, at 24° C., the maximum permissible mixing time is about two hours, at 36° C., the maximum permissible mixing time is about one-half hour.

The chloride ions and yeast material can be mixed together at room temperature and then placed in a cold room, 0°–5° C., or they can be mixed in a cold room.

TABLE VII
EFFECT OF TEMPERATURE FOR MIXING THE REHYDRATED DRIED BAKERS' YEAST ON THE EXTRACTION OF CoA—SPC ACTIVITY

| Mixing Temperature (°C.) | CoA—SPC Activity (nmoles) | Soluble Protein (mg/ml) | Specific Activity (nmoles/mg/h) |
|---|---|---|---|
| 4 | 25.6 | 74 | 6.9 |
| 24 | 0 | 76 | 0 |
| 36 | 0 | 75 | 0 |

*a*Dried Bakers' yeast (34% at the original wet weight) was ground at 24° to a particle size range of 425 to 38 microns and rehydrated at 4° with deionized H₂O. KCl was added to each yeast suspension at a concentration of 10 mg/ml of yeast suspension. Each suspension was mixed at the prescribed temperature (above) for 18 h. The soluble portion was recovered by centrifugation at 10,000 xg for 20 minutes at 4°.

EXAMPLE 8

Table VIII compares CoA-SPC activity obtained using various procedures. In A, the CoA-SPC was simply released from hydrated yeast by adding chloride ions. In this procedure, endogenous t-factor released the CoA-SPC.

In B, the soluble components of the yeast were removed and the CoA-SPC activity was released by adding crude t-factor and chloride ions to the insoluble material. Pure t-factor would be satisfactory but it was not used for this experiment.

In C, water and chloride ions were used to release the CoA-SPC. The released activity is due to residual t-factor that remained with the insoluble material. The insoluble material was not washed free of t-factor.

TABLE VIII
EFFECT OF INITIAL REMOVAL OF THE SOLUBLE PORTION OF FRESH BAKERS' YEAST ON THE EXTRACTION OF CoA—SPC FROM THE REMAINING DRIED SOLID RESIDUE[a]

| Condition | CoA—SPC Activity (nmoles) | Soluble Protein (mg/ml) | Specific Activity (nmoles/mg/h) |
|---|---|---|---|
| A. Control[b] | 23.5 | 68 | 6.9 |
| B. Liquid nitrogen supernatant and dried yeast residue[c] | 58.7 | 170 | 6.9 |
| C. Deionized H₂O + dried yeast residue[d] | 14.9 | 113 | 2.6 |

[a]As described in U.S. Pat. application Ser. No. 900,125, filed April 26, 1978, and Life Sciences 23:2751-2768 1978, the liquid portion of fresh compressed Bakers' yeast can be removed by freezing the fresh Bakers' yeast in liquid nitrogen followed by a thawing period of approximately 4 h. The liquid portion may then be recovered by centrifugation at 10,000 or 105,000 xg for 1 hr at 4°. For Table VIII above, three successive freeze thaw periods were carried out followed by a centrifugation step. Following the centrifugation, the liquid portion was saved and the solids obtained by centrifugation were spread uniformly on glass trays and dried at 24° for 72 h. Occasionally, the residue was turned to enhance drying.
[b]Dried Bakers' yeast (34% of the original wet weight) was ground at 24° to a particle size range of 425 to 38 microns and rehydrated with deionized H₂O at 4°. KCl was added to the suspension at a concentration of 10 mg/ml of yeast suspension. The suspension was mixed at 4° for 18 h. The soluble portion was recovered by centrifugation at 10,000 xg for 20 minutes at 4°.
[c]Dried yeast residue obtained from the insoluble portion of the liquid N₂ freeze-thaw procedure was ground to a particle size of 425 to 38 microns. Supernatant liquid (4°) obtained from the liquid N₂ freeze-thaw procedure was added to the dried residue (9.5 g) to obtain a total volume of 26 ml. KCl was added to a concentration of 10 mg/ml of yeast suspension and mixed for 18 h at 4°. Mixing was followed by centrifugation at 10,000 xg for 20 minutes at 4° to obtain the liquid portion.
[d]Dried yeast residue obtained from the insoluble portion of the liquid N₂ freeze-thaw procedure was ground to a particle size of 425 to 38 microns. Deionized H₂O (4°) was added to the dried yeast residue (9.5 g) to obtain a total volume of 26 ml. KCl was added to a concentration of 10 mg/ml yeast suspension and mixed for 18 h at 4°. Mixing was followed by centrifugation at 10,000 xg for 20 minutes at 4° to obtain the liquid portion.

EXAMPLE 9

Table IX reports the results when storing dried, ground yeast under several conditions. The control sample is the initial CoA-SPC activity before storage.

TABLE IX
EFFECT OF STORAGE CONDITIONS ON THE ABILITY TO OBTAIN AN EXTRACT WITH CoA—SPC ACTIVITY

| Storage Condition[a] | CoA—SPC Activity (nmoles) | Soluble Protein (mg/ml) | Specific Activity (nmoles/mg/h) |
|---|---|---|---|
| Control[b] | 25.6 | 74 | 6.9 |
| Room Temperature | 14.2 | 74 | 3.8 |
| Dessicated | 24.0 | 74 | 6.5 |

[a]Fresh Bakers' yeast dried to approximately 34% weight remaining and stored at room temperature (24°) in a closed container, and another portion was stored in a vacuum dessicator over anhydrous CaCl₂ at 4°. Storage period for the study was four weeks.
[b]For all conditions, the dried yeast was ground to a particle range of 425 to 38 microns, and rehydrated with deionized H₂O at 4°. KCl was added to a concentration of 10 mg/ml yeast suspension and mixed for 18 h at 4°. The liquid portion of the suspension was recovered by centrifugation at 10,000 xg for 20 minutes at 4°.

EXAMPLE 10

Table X demonstrates that the CoA-SPC prepared by the procedure of this invention is equivalent to CoA-SPC prepared by earlier procedures as described in U.S. patent application Ser. No. 727,633, filed Sept. 29, 1976 and U.S. application Ser. No. 900,125, filed Apr. 26, 1978. The difference in counts per minute between the two samples is not significant and are normal sample-to-sample variations.

TABLE X
USE OF THE NEW METHOD FOR THE PREPARATION OF A CoA—SPC EXTRACT IN THE B-PROTEIN ASSAY FOR THE DETECTION OF CANCER[a]

| Method of Preparation of CoA—SPC[b] | Sera Normal (cpm) | Sera Cancer (cpm) |
|---|---|---|
| Ether-solid CO₂ | 390 | 1274 |
| Dry-rehydration | 410 | 1123 |

[a]Details for the B-Protein Assay for the Detection of Cancer can be found in U.S. Pat. application Ser. No. 727,633, filed September 29, 1976, Third International Symposium on the Detection and Prevention of Cancer, 3:275-269, 1976, and IRCS Medical Science 7:71, 1979.
[b]The Ether-solid CO₂ preparation has been described in previous communications: U.S. Pat. application Ser. No. 727,633, filed September 29, 1976, U.S. Pat. application Ser. No. 900,125, filed April 26, 1978, Third International Symposium on the Detection and Prevention of Cancer, 3:257-269, 1976, IRCS Medical Science 6:283, 1978 and Life Sciences 23:2757-2768, 1978.
The Dry-rehydration procedure, utilized herein, consisted of Bakers' yeast dried to approximately 34% weight remaining, ground to a particle size range of 425 to 38 microns and rehydrated with deionized H₂O at 4°. The suspension was mixed with 10 mg/ml yeast suspension at 4° for 18 h. The recovery of the CoA—SPC extract was by centrifugation at 10,000 xg for 20 minutes at 4°.

EXAMPLE 11

Table XI demonstrates how the use of a vacuum can greatly decrease the drying period which is necessary in order to produce an active CoA-SPC material. As can be seen, the use of a 30 psi vacuum at a temperature of 40° C. reduced the drying time to within a range of from 4 to 8 hours while the same vacuum at room temperature reduced the drying time to on the order of from 11 to 18 hours. A comparison of these results with those reported in Table I will reveal that the drying time required at room temperature when using the vacuum is about ⅓ that when a vacuum was not employed. Thus, the use of vacuum drying can greatly decrease the total drying time required.

The experiment with vacuum drying at 4° C. was not successful because the yeast was not dried. It appears that at low temperatures a much greater degree of vacuum is required if drying is to be achieved along with successful lysing of the yeast.

In addition to the lysing procedures specifically exemplified, it is also possible to simply expose the yeast cells to ether alone followed by decantation of the ether and a brief vacuuming period to remove any residual ether. The resulting yeast cells are then treated in accordance with the procedure described in the specification and active CoA-SPC is obtained.

Enzymatic attack on the yeast cells using gut enzymes from the species of snail called *Helix pomatia*. These gut enzymes are available commercially and are called Glusulase. The action of these enzymes cause the formation of spheroplasts; that is, only a portion of the cell wall is lost. The enzymes buffered in combination with chelating agents such as citrate and EDTA and the reducing agent β-mercaptoethanol. After the enzymes have had an opportunity to attack the cell walls, the spheroplasts are washed and then exposed to hypoosmotic conditions, such as distilled water, to produce CoA-SPC. The CoA-SPC activity of the material recovered appears to be lower than that of either the procedure described by Morrison et al or that of the alternative procedures exemplified previously. It is possible that the reduced CoA-SPC activity may be caused by the inhibitory effects of the citrate, the EDTA or the β-mercaptoethanol on the extracted CoA-SPC preparation. It is also possible that the reduced activity may be a result of the ability of the glusulase to attack log phase yeast cells better than stationary phase cells. Commercial Bakers' yeast is generally in the stationary phase.

TABLE XI
DECREASED DRYING PERIODS THROUGH USE OF A VACUUM[a]

| Temperature (°C.) | Time[b] (h) | Activity (nmoles) | Soluble Protein (mg/ml) | Specific Activity (nmoles/mg/h) |
|---|---|---|---|---|
| 40° | 4–8 | 23.5 | 69 | 6.8 |
| 24° | 11–18 | 23.5 | 68 | 6.9 |
| 4°[c] | 24–72 | 0 | 11 | 0 |

[a]Water aspirator pulling a vacuum of 30 psi.
[b]The range of time to obtain 34% original wet weight remaining appears to be related to the initial moisture content of the yeast.
[c]Unable to dry the yeast at this temperature with the vacuum available. If a higher vacuum could have been attained, then an active CoA—SPC extract would have resulted.

EXAMPLE 12

Assay for CoA-SPC Activity

CoA-SPC activity was determined using either L-cysteine, D-pantothenic acid or ATP as the radioactive tracer. A typical reaction mixture contained: 4.70 mM disodium ATP, 0.5 ml buffer A (containing 0.10 M trisacetate, pH 7.2, 0.02 M magnesium acetate 0.05 M KCl), 0.50 mM calcium salt of D-pantothenic acid, 0.50 mM of [$^{35}$S]-L-cysteine (18,000 cpm), 0.05 ml of the supernatant fraction to be assayed and water to a total volume of 1 ml. Reaction mixtures without ATP served for background activity.

Tubes containing the reaction mixture were incubated at 36° C. for one hour. The reaction was terminated by adding 2 ml of 10% TCA and heating the tubes in a boiling water bath for five minutes. The tubes were cooled and the denatured protein precipitates containing the CoA-SPC were recovered by filtration using a Millipore filtering apparatus and Whatman No. 3 MM paper discs. The precipitates collected on the discs were washed four times with approximately 2 ml of water per wash. The discs were dried and then transferred to scintillation vials, and the radioactivity present measured in a Nuclear Chicago Liquid scintillation counter using the scintillation liquid measured by Hoskinson and Khorana in J. Biol. Chem, 240 pages 2129–2135 (1965).

Assay for t-Factor Activity

The assay procedure used to detect the presence of t-factor is as follows:

The fraction to be tested for t-factor activity was stirred for 17 hours at 4° C. with washed pellet material recovered from the crude yeast cell lysate by centrifugation at 105,000×g for 1 hour, and KCl was added to a final concentration of 5 mg/ml. Following the stirring step, the mixture was centrifuged at 105,000×g for one hour, and the supernatant liquid was assayed for CoA-SPC activity as previously described. For control samples pellet material was stirred for 17 hours with 0.05 M Tris-acetate, pH 7.2 containing 5 mg/ml KCl, and with the 105,000×g supernatant fraction in the absence of exogenous KCl.

Preparation of t-Factor

Approximately 454 g of fresh Bakers' yeast were crumbled into a suitable container containing 0.7 kg of anhydrous ethyl ether. Compressed $CO_2$ (3 kg) was added to freeze the yeast. The frozen yeast was thawed at 23°–24° C. for 7 hours. Residual ether and $CO_2$ were removed from the thawed yeast cell lysate by vacuum as previously described in Morrison et al.

The yeast cell lysate was divided into three equal parts and treated according to the following procedures. One-third of the lysate, Procedure I, remained as a crude lysate. The second one-third of the lysate, Procedure II, was centrifuged at 105,000×g for 1 hour and the supernatant saved. The final portion of the yeast cell lysate, Procedure III, was centrifuged at 1,000×g for 10 minutes at 4° C. to remove intact yeast cells. The cells were discarded, and the remaining suspension was centrifuged at 105,000×g for 20 minutes at 4° C. Both pellet and supernatant fraction were saved. The supernatant fraction was heated at 80° C. for five minutes centrifuged at 105,000×g for one hour and decanted through cheesecloth and saved. The pellet material was resuspended two times in 0.05 M Tris-acetate, pH 7.2, and centrifuged successively at 105,000×g for one hour to wash the pellet material. A portion of the washed pellet material, Procedure IIIa, was resuspended in the 105,000×g heated supernatant fraction as in Procedure III. Another portion of the washed pellet material, Procedure IIIb, was suspended in 0.05 M Tris-acetate, pH 7.2. A final concentration of approximately 5 mg/ml of exogenous KCl was added to Procedures I, II, IIIa and IIIb, and mechanical stirring was then initiated and continued at 4° C. for 17 hours.

Following the 17 hour stirring step, which gradually solubilized CoA-SPC, the mixture form Procedure I, II, IIIa, and IIIb were centrifuged at 105,000×g for one hour separating pellet and supernatant fraction. Each supernatant fraction was assayed to CoA-SPAC activity using either L-cysteine, D-pantothenic acid or ATP as the radioactive tracer.

Procedure I and Procedure IIIa contained CoA-SPAC activity as determined by the amount of measurable radioactivity incorporated into the TCA precipitates. Procedure IIIb, which contained washed pellets mixed with 0.05 M Tris-acetate, pH 7.2 and Procedure II, were void of CoA-SPC activity. Consequently, it would appear that a component (s) present in the supernatant fraction is required to solubilize CoA-SPC.

The evidence presented contains two vitally important characteristics of CoA-SPC. (1) CoA-SPC appears to be bound to extremely heavy, insoluble yeast cell component (s), and will remain in that state unless conditions described under Procedure I and Procedure IIIa above are followed; (2) a soluble component of the yeast cell is essential for the release or solubilization of CoA-SPC. Because this soluble cellular component had not been identified, it has tentatively been named t-factor.

EXAMPLE 13

Bakers' yeast (454 g.) is crumbled into liquid $N_2$ to freeze the cells. The frozen cells are then thawed and the thawed mixture contains lysed cells, intact cells and soluble cellulare components from both. This mixture is centrifuged at $105,000 \times g$ at 4° C. for one hour. The liquid fraction is decanted into another vessel and heated at 80° C. for 10 minutes to remove heat denaturable proteins from the mixture. Following the heating procedure, the mixture is centrifuged again at $105,000 \times g$ for 30 minutes. The supernatant liquid obtained is dialysed using No. 8 tubing against reduced pressure, from 700 to 12 mm Hg. All detectable t-factor activity is present in the dialysate. For some preparations an alternate step to dialysis is used. The heated supernatant fraction is filtered, rather than dialyzed, through Amicon Centriflo filter cones (CF25) that retain materials of 25,000 mw or greater. In this case, t-factor appears in the filtrate. Either the dialysate or the filtrate containing t-factor is subjected to two successive ultrafiltration steps. The first ultrafiltration step utilizes an Amicon UM-2 filter (1,000 mw retention). The second ultrafiltration step involves passing the UM-2 filtrate, which contains t-factor, through an Amicon UM-05 membrane (500 mw retention). The t-factor was present in the UM-05 filtrate. On the basis of the ultrafiltration steps, it would appear that t-factor has a molecular weight of 500 or less, however, it is known that certain compounds such as CoA, with a molecular weight of 800 pass through this filter. Column chromatography indicates that the t-factor has a molecular weight of between 400 and 1,000.

CoA-SPC activity has not been demonstrated prior to its solubilization; therefore, testing for t-factor activity is by indirect assay based on the presence of CoA-SPC activity after solubilization. The amount of CoA-SPC activity present after 17 hour stirring appears to be directly related to the concentration of t-factor present in the fraction tested.

EXAMPLE 14

The apparent CoA-SPC solubilizing ability of t-factor may suggest t-factor functions as a proteolytic enzyme. A portion of the Amicon UM-05 filtrate was lyophilized in 4 ml aliquots. One aliquot of the filtrate was dissolved in 10 ml of 0.13 M ammonium bicarbonate, and to this 100 μg of trypsin (Worthington, 2× crystallized) was added. The pH of the solution was adjusted to 8.0 with 1 N $NH_4OH$. A control sample was prepared in a similar manner, except the trypsin was inactivated by boiling for 2 minutes prior to its addition to the lyophilized UM-05 filtrate. Two additional aliquots were subjected to protease (Sigma, Strep. griscus, repurified Type VI) digestion. To one aliquot of the lyophilized filtrate, dissolved in 10 ml of 0.13 M ammonium bicarbonate, 100 μg of protease was added and the pH adjusted to 7.2 with 1 N HCl. A control for protease was prepared identically, except the enzyme was boiled for 2 minutes prior to its addition to the lyophilized UM-05 filtrate. All four samples were incubated 6 hours at 36° C. and the pH monitored. Following the incubation period, the enzymatic reactions were terminated by boiling for 3 minutes. Denatured proteolytic enzymes were removed by centrifugation, and the supernatant liquids were dialyzed at 4° C. against reduced pressure through No. 8 tubing. The dialysates were lyophilized to dryness and dissolved in 4 ml $H_2O$. The pH was adjusted to 5.8, if necessary, with 1 N HCl. Potassium chloride was aded to a final concentration of 5 mg/ml, and the dialysates were mixed with washed pellet material obtained from the $CO_2$-ether preparation method. Assaying for CoA-SPC activity revealed that trypsin and protease controls had activity. In addition, the reaction mixtures in which trypsin and protease had not been inactivated had the same level of CoA-SPC activity. The evidence presented is highly suggestive that t-factor does not contain peptide bonds.

Heat Treatment of t-Factor

The UM-05 filtrate was also tested for stability to heat. Table 1 shows that less than a 10% decrease in t-factor activity was observed after heating at 80° C. for 24 hours. Consequently, it would appear, particularly since the detectable loss in t-factor activity took place during the first 10 minute heating, that t-factor is stable under these conditions. Any observed losses in t-factor activity appears to be due to inherent characteristics of the procedure.

Requirement for KCl or Chloride Ion

Exogenous cloride or nitrate ions and t-factor appear to be essential for maximum solubilization of CoA-SPC (Table XII). Because of the presence of endogenous chloride ions in the fractions containing t-factor, some CoA-SPC activity was detected without the addition of chloride to the stirring flask. However, KCl in $H_2O$ or in 0.05 M tris acetate, pH 7.2 in the absence of t-factor did not release CoA-SPC. It is believed that t-factor is specific for the release of CoA-SPC, however, the amount of protein present in the supernatant fraction following stirring pellet material with t-factor and KCl is greater than the amount of protein which could be accounted for by CoA-SPC alone. Therefore, extraneous protein is also solubilized. It is known that much of the extraneous protein solubilized is due to mechanical stirring and salt concentration.

As demonstrated in Table XII it is the chloride or nitrate ion which appears to be essential for the solubilization of CoA-SPC and not the cation. Mono and dichloride salts at equivalent chloride ion concentrations were shown to function equally as well in the solubilization of CoA-SPC. The addition of salts not containing chloride or nitrate (e.g., KAc, NaAc, $Na_2SO_4$) did not elevate the level of CoA-SPC activity above that indicated for endogenous chloride. Consequently, it would appear that the salts tested not containing chloride or nitrate ions were not functional in the solubilization of CoA-SPC. The chloride or nitrate ions may be added in any conventional form, such as the form of a salt. However, cations such as Li, Hg, Pb, Zn and Fe, appear to inhibit the catalytic activity of CoA-SPC. Cations such as K, Na, Mn, Mg, and Ca have all proven suitable.

In other studies, experiments were conducted using [$^{36}$Cl]-NaCl to determine if the chloride ion exerts its action by binding to CoA-SPC, heavy components of the yeast cell lysate or t-factor. Results of these experiments did not indicate that $^{36}$Cl$^-$ was binding to any of these fractions. Therefore,

TABLE XII

Effect of Various Salts on the Solubilization of CoA—SPC

| Components Added | | CoA—SPC Activity |
|---|---|---|
| t-Factor | Salt | mμ moles |
| + | — | 5.2 |
| + | KCl | 19.8 |
| — | KCl[2] | 0.5 |
| + | NaCl | 18.2 |
| + | MgCl$_2$ | 19.3 |
| + | CaCl$_2$ | 25.0 |
| + | MnCl$_2$ | 29.3 |
| + | LiCl[3] | 0.3 |
| + | KC$_2$H$_3$O$_2$ | 7.6 |
| + | NaC$_2$H$_3$O$_2$ | 4.9 |
| + | KI | 3.1 |
| + | Na$_2$SO$_4$ | 5.2 |
| + | KNO$_3$ | 18.9 |
| + | Ca$_3$(PO$_4$)$_2$ | 0.1 |
| — | CaCl$_2$ | 0.2 |

[1](+) indicate t-factor added, (—) indicate either t-factor or salt is omitted from the mixture.
The average endogenous Cl$^-$ concentration based on several batches of yeast was 0.92 mg/ml of the 105,000 xg supernatant fraction of the cell lysate. The 5 mg/ml of exogenous KCl added is based on the total yeast cell volume. This is equivalent to 25 mg/ml exogenous KCl for the 105,000 xg supernatant fraction. Other salt tested were adjusted to approximately the KCl concentration.
[2]KCl in the absence of t-factor was dissolved in 4 ml of H$_2$O and then mixed with pellet material as described under "Assay for t-Factor Activity".
[3]Anions associated with cations such as Li, Hg, Pb, Zn, Fe appear to inhibit the catalytic activity of CoA—SPC.

if $^{36}$Cl$^-$ binding does take place, the bond between $^{36}$Cl$^-$ and its site of binding is broken during the recovery of CoA-SPC, other cell components or t-factor for assay.

Moreover, t-factor does not appear to exert its action by forming a stable bond with CoA-SPC or other cellular components, because following solubilization of CoA-SPC, t-factor can be recovered several times by dialysis and reused without an apparent loss of activity.

Bakers' yeast cells contain proteolytic enzymes and other enzymes which may be detrimental to CoA-SPC, its substrate or its product—the binding protein. CoA-SPC as prepared in U.S. Application Ser. No. 727,633, filed September 29, 1976, contains substantial quantities of these enzymes and contains detectable levels of Protease A, B and C. The maximum purity which can be obtained with the procedure disclosed in Application Ser. No. 727,633, is about 36 fold. The CoA-SPC of the present invention is purified at least 45 fold, and generally at least 50 fold. Purities of 50 fold are readily obtainable and provide a CoA-SPC which is free of detectable levels of Protease A, B and C. Further, most of the other proteolytic and hydrolytic enzymes whether soluble in vacuoles or in periplasmic spaces are removed by the procedure of this invention to prepare CoA-SPC. Thus, the CoA-SPC Bakers' yeast extract of this invention may be characterized as free of detectable levels of Proteases A, B and C.

The purity of the CoA-SPC is calculated as follows:

$$\frac{\text{counts per minute/mg of purified solution protein}}{\text{counts per minute/mg of crude solution protein}} = \text{fold of purity}$$

wherein the counts per minute/mg of solution protein are determined as described in Example 1; wherein, $$\frac{\text{counts/min/ml of solution}}{\text{mg of protein/ml of solution}} = \text{counts/min/mg of solution protein}$$

If desired, the t-factor may be prepared in a very purified form such that it is essentially free of all proteinaceous materials. Consequently, all detectable proteolytic and other enzymes in the soluble portion of the cell lysate, from which the t-factor has been purified, have been removed. In addition, the procedures of this invention removes from the t-factor the endogenous substrate D-pantothenic acid and L-cysteine as well as all other soluble components with a molecular weight of more than 1,000 and less than 400.

The washing of the solid which results from lysing of the yeast cells followed by salt extraction, as described previously, removes the unwanted and undesirable proteinaceous materials such that CoA-SPC of high purity as discussed previously is obtained. This high purity CoA-SPC has been shown to be stable to lypholization and storage and storage at in solutions at —20° C. After storage for four (4) months, the activity of the CoA-SPC had not decreased from its original level. This represents a significant improvement over the CoA-SPC described in U.S. Application Ser. No. 727,633. The CoA-SPC prepared in accordance with the procedure described in that application loses from 25 to 100% of activity after storage for similar time periods of about four (4) months. Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A process for preparing CoA-SPC Bakers' yeast extract which comprises:
   lysing Bakers' yeast cells;
   separating the Bakers' yeast cell lysate into solid and supernatant fractions wherein said solid fraction is substantially free of t-factor;
   treating said solid fraction to solubilize insoluble proteinaceous material other than the insoluble CoA-SPC;
   separating said solubilized proteinaceous materials from the fraction containing said insoluble CoA-SPC;
   contacting said fraction containing said insoluble CoA-SPC with said supernatant fraction containing t-factor to produce soluble CoA-SPC; and
   wherein said t-factor is characterized by that fraction of Bakers' yeast having a molecular weight of 400 to 1000 and which solubilizes insoluble CoA-SPC in the presence of chloride ions.

2. The process of claim 1, wherein said supernatant fraction containing said t-factor is denatured prior to contact with said insoluble CoA-SPC.

3. The process of claim 2, wherein the denatured proteins are separated from the supernatant fraction prior to contact with said insoluble CoA-SPC.

4. The process of claim 1, wherein said insoluble proteinaceous material is solubilized by contacting said solid fractions with an anion containing aqueous medium.

5. The method of claim 4, wherein said anion concentration is at least 0.01 N.

6. The method of claim 1, wherein substantially all of the proteolytic enzymes are separated from said CoA-SPC prior to solubilizing said CoA-SPC.

7. The process for the preparation of CoA-SPC Bakers' yeast extract which comprises:
    (a) drying Bakers' yeast;
    (b) grinding the dried Bakers' yeast;
    (c) hydrating said ground dried yeast in water to form a suspension;
    (d) separating said suspension into solid and supernatant fractions wherein said solid fraction is substantially free of t-factor;
    (e) treating said solid fraction to solubilize insoluble proteinaceous material other than the insoluble CoA-SPC;
    (f) separating said solubilized proteinaceous materials from the fraction containing said insoluble CoA-SPC;
    (g) contacting said fraction containing said insoluble CoA-SPC with a source of t-factor to produce insoluble CoA-SPC;
    (h) solubilizing and recovering the CoA-SPC; and wherein said t-factor is characterized by that fraction of Bakers' yeast having a molecular weight of 400 to 1000 and which solubilizes insoluble CoA-SPC in the presence of chloride ions.

8. The method of claim 7, wherein said source of t-factor is said supernatant fraction.

9. The process of claim 7, wherein the yeast is dried at a temperature between about 10° C. and 60° C.

10. The process of claim 9, wherein the yeast is dried at a temperature between about 20° C. and 50° C.

11. The process of claims 7, 9 or 10, wherein the Bakers' yeast is hydrated in deionized water at a temperature from about 4° C. to about 40° C.

12. The process of claim 11, wherein the temperature hydration is between about 4° C. and 25° C.

13. The process of claim 11, wherein the amount of deionized water added to the dried yeast powder is from about ½ to 4 times the amount of water removed during the drying of said yeast.

14. The process of claim 8, wherein said supernatant fraction containing said t-factor is denatured prior to contact with said insoluble CoA-SPC.

15. The process of claim 14, wherein the denatured proteins are separated from the supernatant fraction prior to contact with said insoluble CoA-SPC.

16. The process of claim 7, wherein said insoluble proteinaceous material is solubilized by contacting said solid fractions with an anion containing aqueous medium.

17. The method of claim 16, wherein said anion concentration is at least 0.01 N.

18. The method of claim 7, wherein substantially all of the proteolytic enzymes are separated from said CoA-SPC prior to solubilizing said CoA-SPC.

* * * * *